US012781022B2

(12) United States Patent
Sampers et al.

(10) Patent No.: US 12,781,022 B2
(45) Date of Patent: Nov. 3, 2026

(54) POLYPROPYLENE COMPOSITION HAVING IMPROVED RADIATION STABILITY

(71) Applicant: SABIC GLOBAL TECHNOLOGIES B.V., Bergen Op Zoom (NL)

(72) Inventors: Jacques Sampers, St. Odiliënberg (NL); Sarah van Mierloo, Opglabbeek (BE)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 358 days.

(21) Appl. No.: 18/684,033

(22) PCT Filed: Sep. 2, 2022

(86) PCT No.: PCT/EP2022/074473
§ 371 (c)(1),
(2) Date: Feb. 15, 2024

(87) PCT Pub. No.: WO2023/036705
PCT Pub. Date: Mar. 16, 2023

(65) Prior Publication Data

US 2024/0360294 A1 Oct. 31, 2024

(30) Foreign Application Priority Data

Sep. 9, 2021 (EP) .................................... 21195654

(51) Int. Cl.
*C09K 11/06* (2006.01)
*A61L 2/00* (2006.01)
*A61L 2/081* (2026.01)
*C08K 5/053* (2006.01)

(52) U.S. Cl.
CPC .............. *C08K 5/053* (2013.01); *A61L 2/081* (2013.01)

(58) Field of Classification Search
CPC .......... A61L 2/08; C09K 11/00; C08F 210/00
USPC ................. 422/22, 24; 252/301.16; 524/250; 260/88.2
See application file for complete search history.

(56) References Cited

U.S. PATENT DOCUMENTS

| | | | | |
|---|---|---|---|---|
| 3,944,530 A * | 3/1976 | Sugita | C08F 210/06 264/537 |
| 4,873,278 A * | 10/1989 | Nelson | C08K 5/05 524/250 |
| 6,664,317 B2 | 12/2003 | King, III | |
| 7,727,418 B2 * | 6/2010 | Momose | C08K 5/0041 252/301.16 |
| 2021/0388176 A1 | 12/2021 | Metzsch-Zilligen et al. | |

FOREIGN PATENT DOCUMENTS

| | | |
|---|---|---|
| CN | 105273308 A | 1/2016 |
| JP | H08176365 A | 7/1996 |
| WO | 9310175 A1 | 5/1993 |
| WO | 2021043784 A1 | 3/2021 |

OTHER PUBLICATIONS

International Search Report for International Application No. PCT/EP2022/074473, International Filing Date Sep. 2, 2022, Date of Mailing Dec. 5, 2022, 3 pages.
Written Opinion for International Application No. PCT/EP2022/074473, International Filing Date Sep. 2, 2022, Date of Mailing Dec. 5, 2022, 4 pages.

* cited by examiner

*Primary Examiner* — Monzer R Chorbaji
(74) *Attorney, Agent, or Firm* — CANTOR COLBURN LLP

(57) ABSTRACT

The invention relates to a polypropylene composition having improved radiation stability, comprising: a) a propylene polymer present in amount ≥94.0 wt. %; and b) aliphatic alcohol having at least two hydroxyl groups, wherein the aliphatic alcohol may be selected from the group consisting of (i) straight chain $C_5$-$C_{20}$ aliphatic diols, (ii) $C_4$-$C_{30}$ aliphatic cyclic alcohols, (iii) polycarbohydrates. and (iv) branched acyclic diols having at least one hydroxyl group attached to a tertiary carbon atom, and combinations thereof, and c) optionally, one or more further additives. The invention further relates to radiation sterilized articles comprising such polypropylene composition and the use of such polypropylene composition for improving radiation stability of articles that are subjected to radiation.

20 Claims, No Drawings

POLYPROPYLENE COMPOSITION HAVING IMPROVED RADIATION STABILITY

CROSS REFERENCE TO RELATED APPLICATIONS

This application is a National Stage application of PCT/EP2022/074473, filed Sep. 2, 2022, which claims the benefit of European Application No. 21195654.5, filed Sep. 9, 2021, both of which are incorporated by reference in their entirety herein.

FIELD OF INVENTION

The present invention relates to a polypropylene composition having improved radiation stability. The invention further relates to radiation sterilized articles comprising such polypropylene composition, to a process for preparing such radiation sterilized articles and to the use of such polypropylene composition for improving the radiation stability of articles that are subjected to gamma radiation.

BACKGROUND

With the advent of global pandemic situation worldwide, the demand for having sterilized consumer goods, or medical devices have never been so high with stringent requirements from both regulatory authorities as well as from customers. Radiation sterilization is one effective method to carry out sterilization, where sterilization may be carried out using irradiation with electron beam (e-beam) or gamma rays (γ-ray) (also referred to as "gamma radiation"). Typically, such sterilization treatment may be used for sterilizing plastic articles used in hospitals, biological laboratories, manufacturers of medical devices, and by other end-users of sterile equipment. Compared with sterilization with chemical reagents, radiation sterilization offers certain advantages as radiation sterilization does not leave behind any trace residue, which may lead to contamination and affect the product purity. Further, owing to the penetrating power of the radiation beam, radiation based sterilization offer efficient industrial operation of sterilizing a large number of articles under one single operation.

However, it has been observed by several industry practitioners and academic researchers, that gamma/e-beam radiation based sterilization may deteriorate the impact properties of a polymer. For example, it has been observed that post sterilization, the impact properties of articles prepared from polymers such as polypropylene, is adversely affected owing to the degradation of polypropylene. The gamma/e-beam radiation effects on polypropylene is of particular interest, as due to its suitable properties of impact, optical and chemical resistance, polypropylene is used extensively in the healthcare and consumer goods industry where there is an ever increasing requirement of using sterilized products.

In the past, radiation resistant polypropylene compositions have been described in several patent and non-patent scientific literature. For example, the patent U.S. Pat. No. 6,664,317 relates to a polyolefin article, which is free of phenolic antioxidant having incorporated a stabilizing system sufficient to attenuate the deteriorating effect of gamma radiation. The stabilizing system consists of a) one or more hindered amine stabilizers; b) hydroxylamine and nitrone stabilizers; and c) organic phosphites. In another example, the published patent application WO1993010175A1 relates to a stabilizing mixture for plastic, comprising tocopherol and polyhydroxy compound such as ethylene glycol and butylene glycol. Although, the various solutions proposed in these patent literatures are promising, there is still a further desire to improve the radiation stability of polypropylene compositions.

Therefore, it is an object of the present invention to provide a polypropylene composition having excellent radiation stability and which is able to impart to an article prepared from such a composition, minimal reduction of impact properties upon being subjected to gamma radiation or e-beam radiation. It is yet another objective of the present invention to provide radiation sterilized articles prepared from such polypropylene compositions.

DESCRIPTION

Accordingly, one or more objectives of the present invention is achieved by a polypropylene composition, comprising:

a. a propylene polymer; and b. an aliphatic alcohol having at least two hydroxyl groups, wherein the aliphatic alcohol is selected from the group consisting of (i) straight chain $C_5$-$C_{20}$ aliphatic diols, (ii) $C_4$-$C_{30}$ aliphatic cyclic alcohols, (iii) polycarbohydrates, and (iv) branched acyclic diols having at least one hydroxyl group attached to a tertiary carbon atom, and combinations thereof. Preferably, the polypropylene composition, comprises:

a. a propylene polymer present in amount ≥94.0 wt. %, preferably ≥97.0 wt. %, preferably ≥98.0 wt. %, preferably ≥99.0 wt. %, with regard the total weight of the polypropylene composition; and b. an aliphatic alcohol having at least two hydroxyl groups, wherein the aliphatic alcohol is selected from the group consisting of (i) straight chain $C_5$-$C_{20}$ aliphatic diols, (ii) $C_4$-$C_{30}$ aliphatic cyclic alcohols selected from a group consisting of 1,3-cyclobutanediol, 2,2,4,4-tetramethylcyclobutanediol, 1,2-cyclopentanediol, 1,2-cyclohexanediol, 1,3-cyclohexanediol, and 1,4-cyclohexanediol (iii) polycarbohydrates, and (iv) branched acyclic diols having at least one hydroxyl group attached to a tertiary carbon atom, and combinations thereof.

Preferably the polypropylene composition, comprises:

a. a propylene polymer present in amount ≥94.0 wt. %, preferably ≥97.0 wt. %, preferably ≥98.0 wt. %, preferably ≥99.0 wt. %, with regard to the total weight of the polypropylene composition; and b. an aliphatic alcohol having at least two hydroxyl groups present in amount ≤6.0 wt. %, preferably ≤3.0 wt. %, preferably ≤2.0 wt. %, preferably ≤1.0 wt. %, with regard to the total weight of the polypropylene composition, wherein the aliphatic alcohol is selected from the group consisting of (i) straight chain $C_5$-$C_{20}$ aliphatic diols, (ii) $C_4$-$C_{30}$ aliphatic cyclic alcohols selected from a group consisting of 1,3-cyclobutanediol, 2,2,4,4-tetramethylcyclobutanediol, 1,2-cyclopentanediol, 1,2-cyclohexanediol, 1,3-cyclohexanediol, and 1,4-cyclohexanediol, (iii) polycarbohydrates, and (iv) branched acyclic diols having at least one hydroxyl group attached to a tertiary carbon atom, and combinations thereof.

Preferably the polypropylene composition, comprises:

a. a propylene polymer present in amount ≥94.0 wt. %, preferably ≥97.0 wt. %, preferably ≥98.0 wt. %, preferably ≥99.0 wt. %, with regard to the total weight of the polypropylene composition; and b. an aliphatic alcohol having at least two hydroxyl groups present in amount ≤6.0 wt. %, preferably ≤3.0 wt. %, preferably ≤2.0 wt. %, preferably ≤1.0 wt. %, with regard to the total weight of the polypropylene composition, wherein the aliphatic alcohol is selected from the group consisting of (i) straight chain $C_5$-$C_{20}$ aliphatic diols, (ii) polycarbohydrates, and (iii) branched acyclic diols having at least one hydroxyl group attached to a tertiary carbon atom, and combinations thereof.

Preferably the polypropylene composition, comprises:

a. a propylene polymer present in amount ≥94.0 wt. %, preferably ≥97.0 wt. %, preferably ≥98.0 wt. %, preferably ≥99.0 wt. %, with regard to the total weight of the polypropylene composition; and b. an aliphatic alcohol having at least two hydroxyl groups present in amount ≤6.0 wt. %, preferably ≤3.0 wt. %, preferably ≤2.0 wt. %, preferably ≤1.0 wt. %, with regard to the total weight of the polypropylene composition, wherein the aliphatic alcohol is a branched acyclic diols having at least one hydroxyl group attached to a tertiary carbon atom, and combinations thereof.

Advantageously, the polypropylene composition of the present invention demonstrates improved radiation stability with reduced deterioration in mechanical properties and optical properties. In particular the polypropylene composition has reduced deterioration of its impact property, even after being subjected to irradiation with gamma or e-beam radiation.

Aliphatic Alcohol Having at Least Two Hydroxyl Groups

Preferably, the straight chain $C_5$-$C_{20}$ aliphatic diol is selected from the group consisting of 1,2-pentanediol, 2,3-pentanediol, 1,4-pentanediol, and 1,4-hexanediol. Preferably, the $C_4$-$C_{30}$ aliphatic cyclic alcohol is selected from the group consisting of 1,3-cyclobutanediol, 2,2,4,4-tetramethylcyclobutanediol, 1,2-cyclopentanediol, 1,2-cyclohexanediol, 1,3-cyclohexanediol, 1,4-cyclohexanediol, and 1,4-dimethylolcyclohexane.

Preferably, the $C_4$-$C_{30}$ aliphatic cyclic alcohol is selected from the group consisting of 1,3-cyclobutanediol, 2,2,4,4-tetramethylcyclobutanediol, 1,2-cyclopentanediol, 1,2-cyclohexanediol, 1,3-cyclohexanediol, and 1,4-cyclohexanediol. Preferably, the polycarbohydrate is selected from the group consisting of polysaccharides and esterified polysaccharides.

Preferably, the aliphatic alcohol having at least two hydroxyl groups is a branched acyclic diol having at least one hydroxyl group attached to a tertiary carbon atom. The branched acyclic diol may for example be represented by formula I Formula I

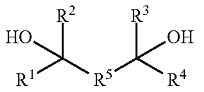

wherein $R^1$, $R^2$, $R^3$, and $R^4$ are each independently selected from the group consisting of hydrogen and an optionally substituted $C_1$-$C_{20}$ alkyl group, preferably wherein at least one hydroxyl group is attached to a tertiary carbon atom and $R^5$ is an optionally substituted $C_1$-$C_{30}$ alkyl group. Preferably $R^1$ and $R^2$ are each not hydrogen or $R^3$ and $R^4$ are each not hydrogen.

Preferably, the branched acyclic diol comprises at least one hydroxyl group attached to a tertiary (3°) carbon atom, wherein the tertiary) (3°) carbon atom may be attached to $R^1$, $R^2$ and $R^5$, provided that $R^1$ and $R^2$ are not hydrogen. Preferably the branched acyclic diol comprises a hydroxyl group attached to a tertiary (3°) carbon atom, wherein the tertiary carbon atom may be attached to $R^3$, $R^4$ and $R^5$, provided that $R^3$ and $R^4$ are not hydrogen.

Preferably, the $C_1$-$C_{20}$ alkyl group is a linear or a branched alkyl group having one to twenty carbon atoms. Preferably, the $C_1$-$C_{20}$ alkyl group is a saturated or an unsaturated alkyl group having one to twenty carbon atoms. Preferably, $C_1$-$C_{20}$ alkyl group is a substituted or an unsubstituted alkyl group having one to twenty carbon atoms. For example, the alkyl group may be substituted by one or more substituents selected from the group consisting of hydroxyl, halogens, nitriles, nitro groups, $C_1$-$C_{20}$ alkyl group, and any combination thereof. Preferably the $C_1$-$C_{20}$ alkyl group is selected from the group consisting of methyl, ethyl, propyl for example iso-propyl, n-propyl; butyl for example iso-butyl, sec-butyl, or n-butyl; pentyl for example iso-pentyl, n-pentyl or sec-pentyl; hexyl, octyl, nonyl, decyl, dodecyl and any combination thereof. Preferably, the $C_1$-$C_{20}$ alkyl group includes at least one of a straight chain alkyl group or a branched alkyl group or a cyclic alkyl group. Preferably, $C_1$-$C_{20}$ alkyl group is a methyl group.

The $R^5$ group may for example be a $C_1$-$C_{30}$ alkyl group. Preferably, the $C_1$-$C_{30}$ alkyl group is a linear or a branched alkyl group having one to thirty carbon atoms. Preferably, the $C_1$-$C_{30}$ alkyl group is a saturated or an unsaturated alkyl group having one to thirty carbon atoms. Preferably, the $C_1$-$C_{30}$ alkyl group is a substituted or an unsubstituted alkyl group having one to thirty carbon atoms. For example, the alkyl group may be substituted by one or more substituents selected from the group consisting of hydroxyl, halogens, nitriles, nitro groups, $C_1$-$C_{30}$ alkyl group, and any combination thereof. Preferably, $R^5$ is selected from —CH2—, —C2H4—, —C3H6—, —C4H8—, —C5H10-group. Preferably, $R^5$ is a methylene group (—CH2—).

Preferably, the aliphatic alcohol is a branched acyclic diol having at least one hydroxyl group attached to a tertiary carbon atom, wherein the aliphatic alcohol is 2-methyl-2,4-pentanediol (hexylene glycol) or 2,3-dimethyl-2,3-butanediol (pinacol). Preferably, the aliphatic alcohol is 2-methyl-2,4-pentanediol (hexylene glycol).

Preferably, the aliphatic alcohol having at least two hydroxyl groups may be present in amount present in amount ≤6.0 wt. %, preferably ≤3.0 wt. %, preferably ≤2.0 wt. %, preferably ≤1.0 wt. %, with regard to the total weight of the polypropylene composition. Preferably, the aliphatic alcohol having at least two hydroxyl groups may be present in amount present in amount >0.0 wt. % and ≤6.0 wt. %, preferably >0.0 wt. % and ≤3.0 wt. %, preferably >0.0 wt. % and ≤2.0 wt. %, preferably >0.0 wt. % and ≤1.0 wt. %, with regard to the total weight of the polypropylene composition.

Preferably, the aliphatic alcohol may be present, in an amount of ≤3.0 wt. %, preferably ≤1.0 wt. %, preferably ≤0.5 wt. % with regard to the total weight of the polypropylene composition. Preferably, the aliphatic alcohol may be present, in an amount of ≥0.05 wt. % and ≤3.0 wt. %, preferably in an amount of ≥0.1 wt. % and ≤1.0 wt. %, preferably in an amount ≥0.1 wt. % and ≤0.5 wt. %, with regard to the total weight of the polypropylene composition.

Propylene Polymer

The propylene polymer may be present in a suitable amount in the polypropylene composition. For example, the propylene polymer may be present in amount ≥94.0 wt. %, preferably ≥97.0 wt. %, preferably ≥98.0 wt. %, preferably ≥99.0 wt. %, with regard to the total weight of the polypropylene composition. Preferably, the propylene polymer may be present in amount ≥94.0 wt. % and <100.0 wt. %, preferably ≥97.0 wt. % and <100.0 wt. %, preferably ≥98.0 wt. % and <100.0 wt. %, preferably ≥99.0 wt. % and <100.0 wt. %, with regard to the total weight of the polypropylene composition.

In some aspects of the invention, the propylene polymer is selected from the group consisting of a propylene homopolymer, a heterophasic propylene copolymer, a propylene copolymer comprising units derived from propylene and one or more units derived from ethylene and/or alpha-olefin(s) having 4-12 carbon atoms, and combinations thereof. Preferably, the propylene polymer is a propylene copolymer comprising units derived from propylene and one or more units derived from ethylene and/or alpha-olefins having 4-12 carbon atoms.

Preferably the alpha-olefin if present in the propylene copolymer, is selected from the group consisting of 1-butene, 1-pentene, 1-hexene, 4-methyl-1-pentene, 1-heptene, 1-octene, 1-decene and 1-dodecene, and combinations thereof. Preferably, the one or more units derived from ethylene and/or alpha-olefins, may for example be present in an amount of ≤10.0 wt. %, for example in an amount of ≥1.0 wt. % and ≤7.0 wt. %, with regard to the total weight of the polypropylene composition, wherein the wt. % is determined using $^{13}C$ NMR.

Preferably, the propylene polymer is a propylene copolymer comprising a random propylene-ethylene copolymer having units derived from propylene and ethylene.

Preferably, the random propylene-ethylene copolymer may has at least one of:

a. a melt flow rate of ≥3.0 and ≤100.0 dg/min, preferably ≥6.0 and ≤90.0 dg/min, wherein the melt flow rate (MFR) is determined using ISO1133:2011 (2.16 kg, 230° C.); and/or
b. an ethylene content of ≥0.5 wt. % and ≤6.0 wt. %, preferably ≥1.5 wt. % and ≤4.5 wt. %, preferably ≥2.0 wt. % and ≤4.0wt %, preferably ≥2.5 wt. % and ≤3.5 wt. %, with regard to the total weight of the random propylene-ethylene copolymer and as determined using $^{13}C$ NMR; and/or
c. a total amount of xylene soluble of ≥1.0 and ≤8.0wt % as determined according to ISO16152:2005; and/or
d. a molecular weight distribution molecular weight distribution (Mw/Mn) of ≥3.0 and ≤10.0, preferably ≥3.5 and ≤8.0, preferably ≥4.0 and ≤7.0, wherein Mw stands for the weight average molecular weight and wherein Mn stands for the number average molecular weight and wherein Mw and Mn are measured by SEC analysis with universal calibration according to ISO16016-1(4): 2003.

Preferably, the random propylene-ethylene copolymer has:

a. a melt flow rate of ≥3.0 and ≤100.0 dg/min, preferably ≥6.0 and ≤90.0 dg/min, wherein the melt flow rate (MFR) is determined using ISO1133:2011 (2.16 kg, 230° C.); and
b. an ethylene content of ≥0.5 wt. % and ≤6.0 wt. %, preferably ≥1.5 wt. % and ≤4.5 wt. %, preferably ≥2.0 wt. % and ≤4.0wt %, preferably ≥2.5 wt. % and ≤3.5 wt. %, with regard to the total weight of the random propylene-ethylene copolymer and as determined using $^{13}C$ NMR; and
c. a total amount of xylene solubles of ≥1.0 and ≤8.0wt % as determined according to ISO16152:2005; and
d. a molecular weight distribution molecular weight distribution (Mw/Mn) of ≥3.0 and ≤10.0, preferably ≥3.5 and ≤8.0, preferably ≥4.0 and ≤7.0, wherein Mw stands for the weight average molecular weight and wherein Mn stands for the number average molecular weight and wherein Mw and Mn are measured by SEC analysis with universal calibration according to ISO16016-1(4): 2003.

The propylene polymers may be prepared by any process known in the art. For example a propylene homopolymer may be obtained by polymerizing propylene monomer under suitable polymerization conditions. As a further example, a propylene copolymer may be obtained by copolymerizing propylene and one or more other comonomers, for example ethylene, under suitable conditions of polymerization. The preparation of propylene homopolymers and propylene copolymers is for example described in Moore, E. P. (1996) Polypropylene Handbook. Polymerization, Characterization, Properties, Processing, Applications, Hanser Publishers: New York. Accordingly, propylene homopolymers, propylene copolymers and heterophasic propylene copolymers may be prepared using any known polymerization technique such as slurry, solution or gas phase polymerizations while the catalyst system that may be used can be Ziegler-Natta, metallocene or single-site catalyst systems. All are, in themselves, known in the art.

Alternatively, the random propylene-ethylene copolymer may be produced under conditions of polymerization as has been described in the published application WO2021043784. In some embodiments, the propylene polymer may be phthalate-containing random polypropylene ethylene copolymer. In some embodiments of the invention the propylene polymer may be phthalate-free random polypropylene ethylene copolymer.

In some aspects of the invention, the polypropylene composition may include a suitable proportion of a propylene polymer and an aliphatic alcohol. For example, the polypropylene composition may comprise:

a. ≥94.0 wt. %, preferably ≥98.0 wt. %, preferably ≥99.0 wt. %, with regard to the total weight of the polypropylene composition, of a propylene polymer, wherein the propylene polymer is a random propylene-ethylene copolymer; and
b. ≤3.0 wt. %, preferably ≤1.0 wt. %, preferably ≤0.5 wt. %, with regard to the total weight of the polypropylene composition, of an aliphatic alcohol having at least two hydroxyl groups, preferably wherein the aliphatic alcohol is 2-methyl-2,4-pentanediol (hexylene glycol).

Additives

In some aspects of the invention, the polypropylene composition may for example contain one or more further additives suitable for imparting specific properties to the polypropylene composition. For example, the polypropylene composition may further comprise one or more additives, wherein the one or more additive is selected from an optical clarifier, an acid scavenger, an anti-static agent, a hindered amine light stabilizer, a non-phenolic processing stabilizer comprising a mixture of a hydroxylamine compound and a phosphite compound, and combination thereof.

The polymer composition may further comprise an optical clarifier to enhance transparency. For example, as an optical clarifier, 1,2,3-tridesoxy-4,6;5,7-bis-O-[(4-propylphenyl) methylene] nonitol sorbitol may be used. For example, 1,2,3-tridesoxy-4,6;5,7-bis-O-[(4-propylphenyl) methylene] nonitol sorbitol (Millad® NX8000 from Milliken) may be used. Preferably, the optical clarifier may be present in an amount of ≥0.05 wt. %, preferably in an amount of ≥ 0.1 wt. %, preferably ≥ 0.05 wt. % and ≤0.40 wt. %, preferably ≥0.10 wt. % and ≤0.30 wt. % with regard to the total weight of the polypropylene composition.

The polymer composition may further comprise an anti-static additive, preferably a glycerol ester, more preferably a mono-ester of a $C_{16}$-$C_{24}$ alkyl acid, for example stearic acid with glycerol. Most preferably, as an antistatic additive Atmer® 129 from Croda (CAS 31566-31-1) is used. The antistatic additive may be present in an amount of ≥0.02 wt. % and ≤0.20 wt. %, preferably from ≥0.080 wt. % and ≤0.12 wt. %, with regard to the total weight of the polypropylene composition.

The polymer composition may further comprise a non-phenolic processing stabilizer. The non-phenolic processing stabilizer may for example be present in an amount of ≥0.02 wt. % and ≤3.0 wt. %, with regard to the total weight of the polypropylene composition. For example, the non-phenolic processing stabilizer comprises a mixture of hydroxylamine and a phosphite compound, preferably a 1:1 mixture of a hydroxylamine and a phosphite compound. Preferably, non-phenolic processing stabilizer is a 1:1 mixture of N,N-dioctadecylhydroxylamine (Irgastab® FS042) and a tris(2,4-di-tert-butylphenyl)phosphite (Irgafos® 168), preferably the non-phenolic processing stabilizer is Irgastab FS 301 from BASF.

The polymer composition may further comprise an acid scavenger, preferably a calcium (Ca) stearate salt. For example, the polymer composition may comprise an acid scavenger in an amount of ≥0.025 wt. % and ≤0.15 wt. %, preferably ≥0.050 and ≤0.10 wt. %, with regard to the total weight of the polypropylene composition.

The polymer composition may further comprise a hindered amine light stabilizer. Preferably the hindered amine light stabilizer is poly[[6-[(1,1,3,3-tetramethylbutyl)amino]-1,3,5-triazine-2,4-diyl][(2,2,6,6-tetramethyl-4-piperidinyl) imino]-1,6 hexanediyl[(2,2,6,6-tetramethyl-4-piperidinyl) imino]]) (Chimasorb 944FD or Sabostab UV94/=HALS). The hindered amine light stabilizer may for example be present in an amount of ≥0.02 wt. % and ≤3.0 wt. % with regard to the total weight of the polypropylene composition.

Preferably, the polypropylene composition comprises at least one of:

a. ≥0.05 wt. % and ≤0.4 wt. % of an optical clarifier;
b. ≥0.02 wt. % and ≤0.2 wt. % of an anti-static additive;
c. ≥0.025 wt. % and ≤0.15 wt. % of an acid scavenger;
d. ≥0.02 wt. % and ≤3.0 wt. % of a hindered amine light stabilizer;
e. ≥0.02 wt. % and ≤3.0 wt. % of a non-phenolic processing stabilizer; and
f. any combination thereof; preferably the total amount of optical clarifier, anti-static additive, acid scavenger, hindered amine light stabilizer, non-phenolic processing stabilizer, is present in an amount ≥0.05 wt. % and ≤3.0 wt. %; preferably in an amount ≥0.05 wt. % and ≤1.0 wt. %; preferably in an amount ≥0.05 wt. % and ≤0.7 wt. %;

with regard to the total weight of the polypropylene composition.

Preferably, the polypropylene composition comprises:

a. ≥0.05 wt. % and ≤0.4 wt. % of an optical clarifier;
b. ≥0.02 wt. % and ≤0.2 wt. % of an anti-static additive;
c. ≥0.025 wt. % and ≤0.15 wt. % of an acid scavenger;
d. ≥0.02 wt. % and ≤3.0 wt. % of a hindered amine light stabilizer;
e. ≥0.02 wt. % and ≤3.0 wt. % of a non-phenolic processing stabilizer; and
f. any combination thereof; preferably the total amount of optical clarifier, anti-static additive, acid scavenger, hindered amine light stabilizer, non-phenolic processing stabilizer, is present in an amount ≥0.05 wt. % and ≤3.0 wt. %; preferably in an amount ≥0.05 wt. % and ≤1.0 wt. %; preferably in an amount ≥0.05 wt. % and ≤0.7 wt. %;

with regard to the total weight of the polypropylene composition.

Preferably the polypropylene composition, comprises:

a. ≥94.0 wt. % and ≤99.9 wt. % of propylene polymer;
b. ≥0.05 wt. % and ≤3.0 wt. % of the aliphatic alcohol having at least two hydroxyl groups; and
c. ≥0.05 wt. % and ≤3.0 wt. % of one or more further additives;

with regard to the total weight of the polypropylene composition.

Advantageously, the polypropylene composition of the present invention may retain its mechanical properties to a considerable extent, in particular its impact property, even after being subjected to a radiation sterilization treatment. For example, the polypropylene composition may after being subjected to irradiation with a gamma radiation dosage of 55 kGy, have a Charpy Impact Strength of not less than 50% of the Charpy Impact Strength of the polypropylene composition prior to irradiation, wherein Charpy Impact Strength is measured in accordance with ISO 179/1eA and within ten days, preferably within seven days of irradiation.

As a further example, the polypropylene composition may after being subjected to irradiation with a gamma radiation dosage of 35 kGy, have a Charpy Impact Strength of not less than 70% of the Charpy Impact Strength of the polypropylene composition prior to irradiation, wherein Charpy Impact Strength is measured in accordance with ISO 179/1eA and within ten days, preferably within seven days of irradiation of irradiation. In other words, the polypropylene composition of the present invention is able to retain a considerable proportion of its impact property even after irradiation, for example at least 70% of its original impact property even when the polypropylene composition is irradiated with a gamma radiation dosage of 35 kGy or at least 50% of its original impact property even when the polypropylene composition is irradiated with a gamma radiation dosage of 55 kGy.

Without wishing to be bound by any specific theory, the inventors believe that a suitable combination of the aliphatic alcohol and the one or more additives impart improved radiation stability to a substantially non-polar propylene polymer. The expression substantially non-polar as used herein means that the propylene polymer does not contain any polar hetero atoms such as an oxygen group.

Radiation Sterilized Article

Accordingly, in some aspects of the invention, the polypropylene composition of the present example relates to the use of the polypropylene composition for improving radiation stability of articles when subjected to radiation sterilization. For example, in some aspects of the present invention, the invention relates to a radiation sterilized article comprising the polypropylene composition of the present invention. The radiation sterilized article may for example be selected from a healthcare article, a food-beverage article, a consumer electronic device. Preferably the radiation sterilized article is a healthcare article selected from a drug delivery article, medical pouch, laboratory ware, a medical device, a medical diagnostics article or a healthcare packaging. Preferably the radiation sterilized article comprises ≥95.0 wt. %, preferably ≥96.0 wt. %, preferably ≥97.0 wt. %, preferably ≥98.0 wt. % with regard to the total weight of the article, of the polypropylene composition of the present invention.

In some aspects of the invention, the invention also relates to a process for preparing the radiation sterilized articles, wherein the process comprises:

a. providing the polypropylene composition of the present invention;
b. processing the polypropylene composition of step (a) and forming a precursor article, wherein processing involves any one of extrusion, injection moulding, blow moulding, melt blending, slush moulding, rotomoulding; and
c. sterilizing the precursor article with radiation and forming the radiation sterilized article.

The radiation that may be used for example be any one of a gamma radiation having a radiation dose of ≥30 kGy and ≤65 kGy, or an electron beam radiation having a radiation dose of ≥25 kGy and ≤45 kGy.

Specific examples demonstrating some of the embodiments of the invention are included below. The examples are for illustrative purposes only and are not intended to limit the invention. It should be understood that the embodiments and the aspects disclosed herein are not mutually exclusive and such aspects and embodiments can be combined in any way. Those of ordinary skill in the art will readily recognize parameters that can be changed or modified to yield essentially the same results.

EXAMPLES

Purpose: For the purposes of exemplifying the present invention, five polypropylene compositions and corresponding samples were prepared. and Their impact properties were evaluated prior to irradiation treatment and post gamma or e-beam irradiation.

For the purposes of the example in this disclosure, the impact properties of the sample (IE) prepared from the inventive polypropylene composition (IE) was compared with that of the comparative compositions (CE1-CE5). Comparative example CE3 represents an unstabilized polypropylene composition while comparative example CE4 represents a polypropylene composition having polyethylene glycol (PEG E9000) as one of the stabilizers. Comparative example CE5 is Bormed™ RF830MO: a polypropylene random copolymer from Borealis intended for evaluation in healthcare application.

Material: The materials used in preparing the formulations are provided under Table 1:

TABLE 1

| Material details | | |
|---|---|---|
| Component | Material | Grade |
| Propylene polymer | Propylene ethylene random copolymer | The grade used is identical to the random polypropylene ethylene copolymer (PP01) prepared in the polymerization process as described in the examples of WO2021043784A1. |
| Aliphatic alcohol | 2-methyl-2,4-pentanediol | Prepared internally at SABIC laboratory |
| Opitcal clarifier | 1,2,3-tridesoxy-4,6,5,7-bis-O-[(4-propylphenyl) methylene] nonitol sorbitol | Millad ® NX8000 of Milliken |
| Anti-static additive | Glycerol monostearate | Atmer ® 129 |
| Acid scavenger | Clacium stearate | |
| Hindered amine light stabilizer | poly[[6-[1,1,3,3 tetramethylbutyl)amino]-s-triazine-2,4-diyl][2,2,6,6-tetramethyl-4-piperidinyl)imino] hexamethylene[(2,2,6,6-tetramethyl-4-piperidinyl) imino]] | Chimassorb ®944 of BASF. |
| Non-phenolic processing stabilizer | combination of hydroxylamine N,N-dioctadecylhydroxyamine (Irgastab ® FS042) and tris(2,4-di-tert-butylphenyl)phosphite (Irgafos ® 168) | Irgastab ® FS301 of BASF |
| Phosphite compound: | tris(2,4-di-tert-butylphenyl)phosphite | Irgafos ® 168 of BASF |
| Phenolic antioxidant: | pentaerythritol tetrakis (3-(3,5-di-tert-butyl-4-hydroxyphenyl)propionate) | Irganox ® 1010 of BASF |
| Polyethylene Glycol | PEG E9000 | |

The details of the formulation are as provided below:

TABLE 2

| Composition details | | | | | |
|---|---|---|---|---|---|
| Sample | IE (Inventive) | CE1 (Comparative) | CE2 (Comparative) | CE3 (Comparative) | CE4 (Comparative) |
| Propylene polymer (wt. %) | 99.199 | 99.499 | 99.399 | 100 | 99.099 |
| Aliphatic alcohol (wt. %) | 0.2* | 0.0 | 0.0 | 0.0 | — |
| Optical clarifier (wt. %) | 0.226 | 0.226 | 0.226 | 0.0 | 0.226 |
| Anti-static additive (wt. %) | 0.1 | 0.1 | 0.1 | 0.0 | 0.1 |
| Acid scavenger (wt. %) | 0.075 | 0.075 | 0.075 | 0.0 | 0.075 |
| Hindered amine light stabilizer (wt. %) | 0.1 | 0.0 | 0.1 | 0.0 | 0.1 |
| Non-phenolic processing stabilizer (wt. %) | 0.1 | 0.0 | 0.1 | 0.0 | 0.1 |
| Phosphite compound (wt. %) | 0.0 | 0.05 | 0.0 | 0.0 | — |
| Phenolic antioxidant (wt. %) | 0.0 | 0.05 | 0.0 | 0.0 | — |
| Polyethylene Glycol (wt. %) | 0.0 | 0.0 | 0.0 | 0.0 | 0.3 (PEG E9000) |

*For the inventive composition (IE), the aliphatic alcohol was introduced as a 2.0 wt. % of a 10.0 wt. % polypropylene masterbatch.

Process for preparing the polypropylene formulations: Compounding was carried out on a KraussMaffei Berstorff pilot extruder with a compounding screw using ZE25/43D. Polypropylene reactor powder 40RG0480 was extruded at a set temperature of 210° C. while additives were introduced via Brabender feeders with a specific output. For the purpose of incorporating the liquid additives without liquid dosing possibilities, powder fluffs were prepared by solvent blending in the laboratory. Liquid additives were dissolved in a suitable solvent and then soaked into the polymer powder homogeneously. After evaporation of the solvent overnight a free flowing powder containing the specific additive was obtained.

For the inventive example (IE), hexylene glycol was prepared as 10.0 wt. % powder fluff with ethanol. All investigated specimens/samples were made by injection molding.

Process for radiation: All radiations were performed by an external company, BGS, located in Whiel, Germany. Three settings were chosen, e-beam with a 40 kGy dose and gamma radiation with dose of 35 kGy and 55 kGy. Dosimeters were added to the samples to ensure that the requested dose was applied. For each formulation, at least 5 specimens were irradiated.

Conducting Charpy Impact Tests: ISO527-1A tensile bars (150*10*4 mm) were injection molded and notched Charpy bars were prepared from these tensile bars. Charpy tests were performed according to standard ISO179/1eA (II).

Results: The results of the Charpy Impact strength tests are as provided below:

TABLE 3

| Charpy Impact Strength Test results | | | | | | |
|---|---|---|---|---|---|---|
| | IE | CE1 | CE2 | CE3 | CE4 | CE5 |
| Charpy Impact Strength (no irradiation) | 5.1 | 4.7 | 4.5 | 4.5 | 5.0 | 4.7 |
| Charpy Impact Strength (after 35 kGy gamma radiation) | 3.7 | 3.0 | 2.4 | 1.0 | 2.9 | 1.6 |
| Charpy Impact Strength (after 55 kGy gamma radiation) | 2.7 | 1.5 | 1.6 | 1.9 | 2.1 | 1.00 |
| Charpy Impact Strength (after 40 kGy e-beam) | 3.9 | 3.8 | 3.2 | NA | 3.2 | 3.8 |

The extent of impact property retained by the samples prepared from the polypropylene compositions is as provided in the table below:

TABLE 4

| Impact property retained | | | | | | |
|---|---|---|---|---|---|---|
| | IE | CE1 | CE2 | CE3 | CE4 | CE5 |
| Original Charpy Impact (%) (no irradiation) | 100 | 100 | 100 | 100 | 100 | 100 |

TABLE 4-continued

| | Impact property retained | | | | | |
|---|---|---|---|---|---|---|
| | IE | CE1 | CE2 | CE3 | CE4 | CE5 |
| Charpy Impact Strength of sample after irradiation with 35 kGy gamma radiation retained (%) | ~72 | ~63 | ~52 | ~22 | ~58 | ~34 |
| Charpy Impact Strength of sample after irradiation with 55 kGy gamma radiation retained (%) | ~52 | ~31 | ~35 | ~19 | ~42 | ~21 |

From Table 4 it is evident that the sample (IE) prepared using the inventive polypropylene composition (IE) is able to retain ~72% (3.7/5.1) of its original impact strength even after the sample (IE) is subjected to 35 kGy gamma radiation. This is in contrast to the sample (CE3) prepared from the unstabilized polypropylene composition (CE3) where the sample (CE3) after 35 kGy gamma radiation is able to retain merely ~22% (1/4.5) of its original impact strength. For the sample (CE4) prepared from the composition having PEG stabilizer (CE4), the composition post irradiation treatment had merely 58% of the original impact strength. In addition, the samples prepared from the polypropylene composition of the present invention demonstrates improved stability towards gamma radiation stability compared with the healthcare grade polypropylene composition Bormed™ RF830MO (72.45% versus 34% for 35 kGy gamma radiation and ~52% versus 21% for 55 kGy gamma radiation).

The results are even more surprising when higher radiation dosage of 55 kGy was used where the sample (IE) prepared from the inventive composition after being subjected to gamma radiation had ~52% of its original impact strength whereas the sample (CE3) prepared from the unstabilized composition CE3 was able to retain merely ~19% of its original impact strength. Even more surprisingly, the sample (IE) prepared from inventive composition (IE) was able to demonstrate a far higher retention of impact strength compared to samples prepared from the comparative composition CE1 and CE2, which use a combination of some of the ordinary stabilizers available commercially. From the results provided, it is also evident that the composition of the invention provides an improved radiation stability to articles in terms of minimizing deterioration of impact properties compared to when polyethylene glycol was used with the propylene polymer (CE4).

The invention claimed is:

1. A polypropylene composition, comprising:

a. a propylene polymer present in amount ≥94.0 wt. %, with regard the total weight of the polypropylene composition; and b. an aliphatic alcohol having at least two hydroxyl groups, wherein the aliphatic alcohol is selected from the group consisting of (i) straight chain $C_5$-$C_{20}$ aliphatic diols, (ii) $C_4$-$C_{30}$ aliphatic cyclic alcohols selected from a group consisting of 1,3-cyclobutanediol, 2,2,4,4-tetramethylcyclobutanediol, 1,2-cyclopentanediol, 1,2-cyclohexanediol, 1,3-cyclohexanediol, and 1,4-cyclohexanediol, (iii) polycarbohydrates, and (iv) branched acyclic diols having at least one hydroxyl group attached to a tertiary carbon atom, and combinations thereof, wherein the propylene polymer is a propylene copolymer comprising a random propylene-ethylene copolymer having units derived from propylene and ethylene, and wherein the random propylene-ethylene copolymer has at least one of:

a melt flow rate of ≥3.0 and ≤100.0 dg/min, wherein the melt flow rate (MFR) is determined using ISO1133: 2011 (2.16 kg, 230° C.); and/or an ethylene content of ≥0.5 wt. % and ≤ 6.0 wt. %, with regard to the total weight of the random propylene-ethylene copolymer and as determined using $^{13}C$ NMR; and/or a total amount of xylene soluble of ≥1.0 and ≤8.0wt % as determined according to ISO16152:2005; and/or a molecular weight distribution (Mw/Mn) of ≥3.0 and ≤10.0, wherein Mw stands for the weight average molecular weight and wherein Mn stands for the number average molecular weight and wherein Mw and Mn are measured by SEC analysis with universal calibration according to ISO16016-1 (4):2003.

2. The polypropylene composition according to claim 1, wherein the aliphatic alcohol is present in an amount of ≤3.0 wt. %, with regard to the total weight of the polypropylene composition.

3. The polypropylene composition according to claim 1, wherein the aliphatic alcohol having at least two hydroxyl groups is a branched acyclic diol having at least one hydroxyl group attached to a tertiary carbon atom, wherein the branched acyclic diol is represented by formula I

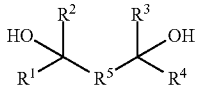

wherein $R^1$, $R^2$, $R^3$, and $R^4$ are each independently selected from the group consisting of hydrogen and an optionally substituted $C_1$-$C_{20}$ alkyl group, and $R^5$ is an optionally substituted $C_1$-$C_{30}$ alkyl group.

4. The polypropylene composition according to claim 1, wherein the aliphatic alcohol is a branched acyclic diol having at least one hydroxyl group attached to a tertiary carbon atom, wherein the aliphatic alcohol is 2-methyl-2,4-pentanediol (hexylene glycol) or 2,3-dimethyl-2,3-butanediol (pinacol).

5. The polypropylene composition of claim 4, wherein the aliphatic alcohol is 2-methyl-2,4-pentanediol (hexylene glycol).

6. The polypropylene composition according to claim 1, wherein the polypropylene composition comprises:

a. ≥94.0 wt. %, with regard to the total weight of the polypropylene composition, of a propylene polymer, wherein the propylene polymer is a random propylene-ethylene copolymer; and b. ≤3.0 wt. %, with regard to the total weight of the polypropylene composition, of an aliphatic alcohol having at least two hydroxyl groups.

7. The polypropylene composition according to claim 1, wherein the polypropylene composition, comprises:

a. ≥94.0 wt. % and ≤99.9 wt. % of propylene polymer;

b. ≥0.05 wt. % and ≤3.0 wt. % of the aliphatic alcohol having at least two hydroxyl groups; and c. ≥0.05 wt. % and ≤3.0 wt. % of one or more further additives;

with regard to the total weight of the polypropylene composition.

8. The polypropylene composition according to claim 1, wherein the polypropylene composition after being subjected to irradiation with a gamma radiation dosage of 55 kGy, has a Charpy Impact Strength of not less than 50% of the Charpy Impact Strength of the polypropylene composition prior to irradiation, wherein Charpy Impact Strength is measured in accordance with ISO 179/1eA and within ten days of irradiation.

9. The polypropylene composition according to claim 1, wherein the polypropylene composition after being subjected to irradiation with a gamma radiation dosage of 35 kGy, has a Charpy Impact Strength of not less than 70% of the Charpy Impact Strength of the polypropylene composition prior to irradiation, wherein Charpy Impact Strength is measured in accordance with ISO 179/1eA and within ten days of irradiation.

10. A radiation sterilized article comprising the polypropylene composition according to claim 1, wherein the radiation sterilized article is selected from a healthcare article, a food-beverage article, a consumer electronic device, preferably the radiation sterilized article is a healthcare article selected from a drug delivery article, laboratory ware, a medical pouch, a medical device, a medical diagnostics article or healthcare packaging.

11. A process for preparing the radiation sterilized article according to claim 10, wherein the process comprises:

a. providing the polypropylene composition;

b. processing the polypropylene composition of step (a) and forming a precursor article, wherein processing involves any one of extrusion, injection moulding, blow moulding, melt blending, slush moulding, rotomoulding; and c. sterilizing the precursor article with radiation and forming the radiation sterilized article.

12. A polypropylene composition, comprising:

a. a propylene polymer present in amount ≥94.0 wt. %, with regard the total weight of the polypropylene composition; and b. an aliphatic alcohol having at least two hydroxyl groups, wherein the aliphatic alcohol is selected from the group consisting of (i) straight chain $C_5$-$C_{20}$ aliphatic diols, (ii) $C_4$-$C_{30}$ aliphatic cyclic alcohols selected from a group consisting of 1,3-cyclobutanediol, 2,2,4,4-tetramethylcyclobutanediol, 1,2-cyclopentanediol, 1,2-cyclohexanediol, 1,3-cyclohexanediol, and 1,4-cyclohexanediol, (iii) polycarbohydrates, and (iv) branched acyclic diols having at least one hydroxyl group attached to a tertiary carbon atom, and combinations thereof, wherein the polypropylene composition further comprises one or more additives, and wherein the one or more additive is selected from an optical clarifier, an acid scavenger, a hindered amine light stabilizer, a non-phenolic processing stabilizer comprising a mixture of a hydroxylamine compound and a phosphite compound, and combinations thereof, an anti-static agent in an amount of ≥0.02 wt. % and ≤0.2 wt. %, with regard to the total weight of the polypropylene composition, or a combination thereof.

13. The polypropylene composition according to claim 12, wherein the propylene polymer is selected from the group consisting of a propylene homopolymer, a heterophasic propylene copolymer, a propylene copolymer comprising units derived from propylene and one or more units derived from ethylene and/or alpha-olefin(s) having 4-12 carbon atoms, and combinations thereof.

14. The polypropylene composition according to claim 12, wherein the propylene polymer is a propylene copolymer comprising a random propylene-ethylene copolymer having units derived from propylene and ethylene, and wherein the random propylene-ethylene copolymer has at least one of:

a. a melt flow rate of ≥3.0 and ≤100.0 dg/min, wherein the melt flow rate (MFR) is determined using ISO1133:2011 (2.16 kg, 230° C.); and/or b. an ethylene content of ≥0.5 wt. % and ≤6.0 wt. %, with regard to the total weight of the random propylene-ethylene copolymer and as determined using $^{13}C$ NMR; and/or c. a total amount of xylene soluble of ≥1.0 and ≤ 8.0wt % as determined according to ISO16152:2005; and/or d. a molecular weight distribution (Mw/Mn) of ≥3.0 and ≤10.0, wherein Mw stands for the weight average molecular weight and wherein Mn stands for the number average molecular weight and wherein Mw and Mn are measured by SEC analysis with universal calibration according to ISO16016-1 (4):2003.

15. The polypropylene composition according to claim 12, wherein the polypropylene composition comprises at least one of:

a. ≥0.05 wt. % and ≤0.4 wt. % of an optical clarifier;

b. ≥0.02 wt. % and ≤0.2 wt. % of an anti-static additive;

c. ≥0.025 wt. % and ≤0.15 wt. % of an acid scavenger;

d. ≥0.02 wt. % and ≤3.0 wt. % of a hindered amine light stabilizer;

e. ≥0.02 wt. % and ≤3.0 wt. % of a non-phenolic processing stabilizer; and f. any combination thereof;

with regard to the total weight of the polypropylene composition.

16. The polypropylene composition of claim 15, wherein a total amount of the optical clarifier, the anti-static additive, the acid scavenger, the hindered amine light stabilizer, the non-phenolic processing stabilizer is ≥0.05 wt. % and ≤3.0 wt. %.

17. The polypropylene composition according to claim 12, wherein the polypropylene composition comprises at least one of:

a. ≥0.05 wt. % and ≤0.4 wt. % of an optical clarifier;

b. ≥0.025 wt. % and ≤0.15 wt. % of an acid scavenger;

c. ≥0.02 wt. % and ≤3.0 wt. % of a hindered amine light stabilizer;

d. ≥0.02 wt. % and ≤3.0 wt. % of a non-phenolic processing stabilizer; and e. any combination thereof;

with regard to the total weight of the polypropylene composition.

18. The polypropylene composition according to claim 12, wherein the polypropylene composition comprises:

a. ≥0.05 wt. % and ≤0.4 wt. % of an optical clarifier;

b. ≥0.025 wt. % and ≤0.15 wt. % of an acid scavenger;

c. ≥0.02 wt. % and ≤3.0 wt. % of a hindered amine light stabilizer; and d. ≥0.02 wt. % and ≤3.0 wt. % of a non-phenolic processing stabilizer;

with regard to the total weight of the polypropylene composition.

19. The polypropylene composition according to claim 12, wherein the polypropylene composition comprises:

a. ≥0.05 wt. % and ≤0.4 wt. % of an optical clarifier;

b. ≥0.02 wt. % and ≤0.2 wt. % of an anti-static additive;

c. ≥0.025 wt. % and ≤0.15 wt. % of an acid scavenger;

d. ≥0.02 wt. % and ≤3.0 wt. % of a hindered amine light stabilizer; and
e. ≥0.02 wt. % and ≤3.0 wt. % of a non-phenolic processing stabilizer;

with regard to the total weight of the polypropylene composition.

20. A polypropylene composition, comprising:

a. a propylene polymer present in amount ≥94.0 wt. %, with regard the total weight of the polypropylene composition; and
b. an aliphatic alcohol having at least two hydroxyl groups, wherein the aliphatic alcohol is selected from the group consisting of (i) straight chain $C_5$-$C_{20}$ aliphatic diols, (ii) $C_4$-$C_{30}$ aliphatic cyclic alcohols selected from a group consisting of 1,3-cyclobutanediol, 2,2,4,4-tetramethylcyclobutanediol, 1,2-cyclopentanediol, 1,2-cyclohexanediol, 1,3-cyclohexanediol, and 1,4-cyclohexanediol, (iii) polycarbohydrates, and (iv) branched acyclic diols having at least one hydroxyl group attached to a tertiary carbon atom, and combinations thereof, wherein the polypropylene composition after being subjected to irradiation with a gamma radiation dosage of 55 kGy, has a Charpy Impact Strength of not less than 50% of the Charpy Impact Strength of the polypropylene composition prior to irradiation, after being subjected to irradiation with a gamma radiation dosage of 35 kGy, has a Charpy Impact Strength of not less than 70% of the Charpy Impact Strength of the polypropylene composition prior to irradiation, or a combination thereof, wherein Charpy Impact Strength is measured in accordance with ISO 179/1eA and within ten days of irradiation.

* * * * *